(12) United States Patent
Kano et al.

(10) Patent No.: US 6,365,021 B1
(45) Date of Patent: Apr. 2, 2002

(54) OXYGEN SENSOR

(75) Inventors: Koji Kano; Koichi Shimamura; Mitsuo Kusa, all of Saitama (JP)

(73) Assignee: Honda Giken Kogyo Kabushiki Kaisha, Tokyo (JP)

( * ) Notice: Subject to any disclaimer, the term of this patent is extended or adjusted under 35 U.S.C. 154(b) by 0 days.

(21) Appl. No.: 09/348,640

(22) Filed: Jul. 6, 1999

(30) Foreign Application Priority Data

Jul. 6, 1998 (JP) .......................................... 10-190544

(51) Int. Cl.$^7$ ............................................. G01N 27/407
(52) U.S. Cl. ....................... 204/426; 204/425; 204/429; 205/785
(58) Field of Search ................................ 204/421–429; 205/785

(56) References Cited

U.S. PATENT DOCUMENTS

| | | | |
|---|---|---|---|
| 4,505,807 A | * | 3/1985 | Yamada |
| 4,579,643 A | * | 4/1986 | Mase et al. |
| 4,657,659 A | * | 4/1987 | Mase et al. |
| 5,366,611 A | * | 11/1994 | Ioannou et al. |

FOREIGN PATENT DOCUMENTS

JP          U 32256        1/1991

* cited by examiner

Primary Examiner—T. Tung
(74) Attorney, Agent, or Firm—Birch, Stewart, Kolasch & Birch, LLP

(57) ABSTRACT

A detecting element is configured such that a second electrode is disposed on one side of a plate-like first electrode with a first solid electrolyte layer positioned therebetween and a third electrode is disposed on the other side of the first electrode with a second solid electrolyte layer positioned therebetween, thereby detecting migration of oxygen ions between the first electrode and the second electrode and migration of oxygen ions between the first electrode and the third electrode. Since the second electrode is disposed on one side of the plate-like first electrode with the first solid electrolyte layer positioned therebetween and the third electrode is disposed on the other side of the first electrode with the second solid electrolyte layer positioned therebetween, both planes of the detecting element functions as detecting planes and, to thus extend the directivity of detection in two directions. Since either the second electrode or the third electrode faces to the flow of exhaust gas, the inventive oxygen sensor can be brought in contact with exhaust gas earlier than a prior art oxygen sensor does. Accordingly, the response time of the inventive oxygen sensor becomes shorter than that of the prior art oxygen sensor.

10 Claims, 6 Drawing Sheets

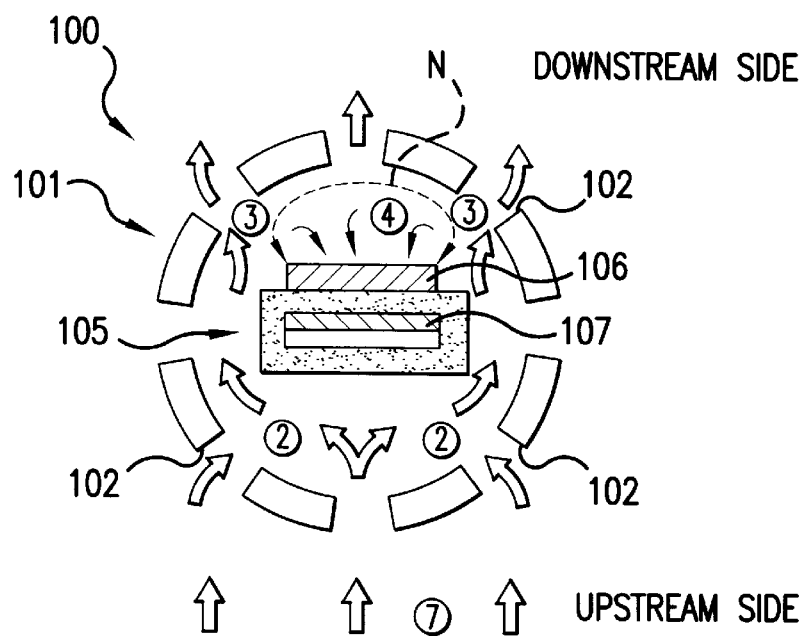
FIG.6(a) COMPARATIVE EXAMPLE
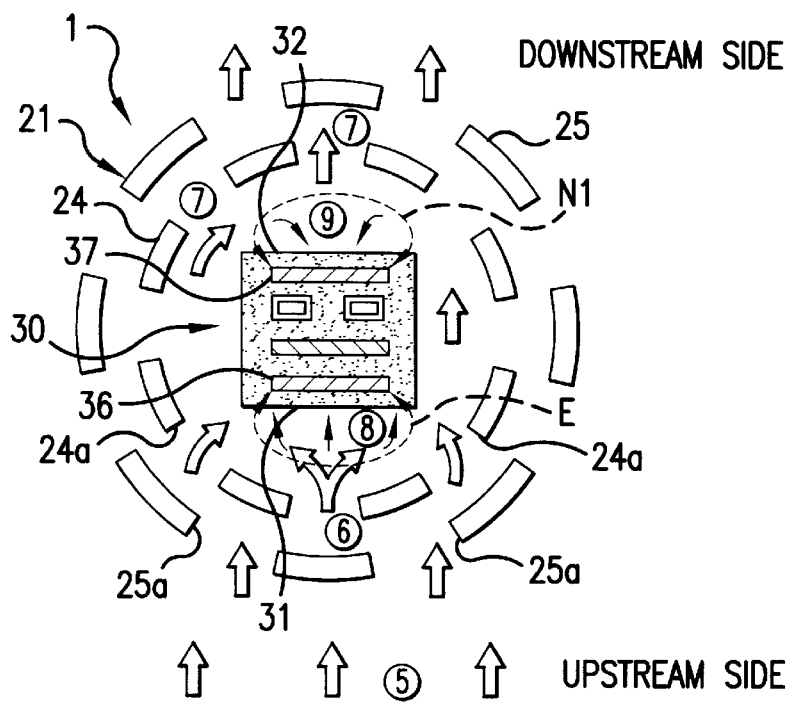
FIG.6(b) EMBODIMENT

OXYGEN SENSOR

BACKGROUND OF THE INVENTION

1. Field of the Invention

The present invention relates to an oxygen sensor for detecting the concentration of oxygen contained in exhaust gas.

2. Description of Background Art

Most oxygen sensors are used for an air-fuel ratio control in industrial furnaces, boilers, and internal combustion engines.

Oxygen sensors, which make use of the principle of a cell, are classified into two types: one being intended to measure an electromotive force generated by chemical reaction of a cell portion of the oxygen sensor, and the other being intended to measure a change in conductance caused by applying a voltage to a solid electrolyte of a cell portion of the oxygen sensor. The former oxygen sensor is known, for example, from Japanese Utility Model Laid-open No. Hei 3-2256 entitled "Oxygen Sensor for Internal Combustion Engine." The configuration of the prior art oxygen sensor disclosed in this document will be described below. Referring to FIG. 1 of this Japanese Utility Model, a protector for protecting a sensor element unit 5 (the following reference numerals are used in the Japanese Utility Model application) is of a double cylinder structure having an outer cylinder 21 and an inner cylinder 22. Exhaust gas inlet holes 21a and exhaust gas introduction holes 22a are formed in peripheral walls of the outer cylinder 21 and the inner cylinder 22, respectively (see FIG. 2), and an exhaust gas outlet hole 22b is formed in a leading end plane of the inner cylinder 22.

Exhaust gas flows in the outer cylinder 21 through the exhaust gas inlet holes 21a. The flow of the exhaust gas is turned in a gap between the outer cylinder 21 and the inner cylinder 22 to be mixed with each other. The mixed exhaust gas flows in the inner cylinder 22 through the exhaust gas introduction holes 22a toward an electrode plane 5a having a directivity, and is then discharged from the exhaust gas outlet hole 22b. The exhaust gas is impinged on the electrode plane 5a along a specific direction irrespective of the orientation of the electrode plane 5a, so that the oxygen sensor can exhibit a constant oxygen concentration detecting performance.

The prior art oxygen sensor having the above structure, however, has problems. Since one side edge of each of the exhaust gas inlet holes 21a of the outer cylinder 21 is inwardly bent, the shape of the hole 21a is complicated, to increase the machining cost of the holes 21a.

Since the gap is large enough to allow turning of exhaust gas therein between the outer cylinder 21 and the inner cylinder 22, the outside diameter of the outer cylinder 21 becomes large and thereby the size of the protector is increased. Also since the flow of exhaust gas is turned to be mixed with each other, it may take an excessive time until the exhaust gas reaches the electrode plane 5a.

The prior art oxygen sensor has another problem in that the inner space of the inner cylinder 22 on the electrode plane 5a side (front side) is smaller than that on the opposed side (back side), so that if exhaust gas flows in the inner cylinder 22 from both the sides as shown in FIG. 3, the exhaust gas exhibits a high fluidity on the back side while it exhibits a poor fluidity on the front side, that is, on the electrode plane 5a side, whereby the responsivity of detection becomes poor. The prior art oxygen sensor, therefore, has room for improvement in terms of responsivity of detection. Since the responsivity of an oxygen sensor exerts a large effect on the performance of an exhaust gas purifying system, it is expected to improve the performance of the oxygen sensor more than ever.

SUMMARY AND OBJECTS OF THE INVENTION

An object of the present invention, therefore, is to provide an oxygen sensor excellent in responsivity of detection.

To achieve the above object, according to the present invention, there is provided an oxygen sensor mounted in an exhaust passage of an engine for detecting an oxygen component contained in exhaust gas, including: a sensor element unit including a plate-like first electrode; a second electrode disposed on one side of the first electrode with a solid electrolyte layer put therebetween; and a third electrode disposed on the other side of the first electrode with a solid electrolyte layer put therebetween, thereby detecting migration of oxygen ions between the first electrode and the second electrode and migration of oxygen ions between the first electrode and the third electrode.

Since the second electrode is disposed on one side of the plate-like first electrode with a solid electrolyte layer put therebetween and the third electrode is disposed on the other side of the first electrode with a solid electrolyte layer put therebetween, both the sides of the sensor element unit function as detecting planes. This means that the directivity of the oxygen sensor extends in two directions. Since either the second electrode or the third electrode faces to the flow of exhaust gas, the oxygen sensor of the present invention can be brought into contact with exhaust gas earlier than the prior art oxygen sensor does. Accordingly, the response time of the oxygen sensor of the present invention becomes shorter than that of the prior art oxygen sensor.

According to the present invention, in addition to the configuration of the invention described above, a plate heater having an opening portion allowing permeation of the oxygen ions therethrough is interposed in at least one of the spaces wherein one of which is between the first electrode and the second electrode and the other of which is between the first electrode and the third electrode.

Since the opening portion allowing permeation of oxygen ions therethrough is formed in the plate-like heater, if the plate-like heater is disposed on the second electrode side, oxygen ions migrate from the second electrode to the first electrode through the opening portion, to generate a current; while if the plate-like heater is disposed on the third electrode side, oxygen ions migrate from the third electrode to the first electrode through the opening portion, to generate a current. As a result, although the plate-like heater is provided in the sensor element unit, any reduction in detecting performance is not reduced.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The present invention will become more fully understood from the detailed description given hereinbelow and the accompanying drawings which are given by way of illustration only, and thus are not limitative of the present invention, and wherein:

FIGS. 6(a) and 6(b) are diagrams illustrating a first function of the oxygen sensor of the present invention.

DETAILED DESCRIPTION OF THE PREFERRED EMBODIMENTS

Figure 1:
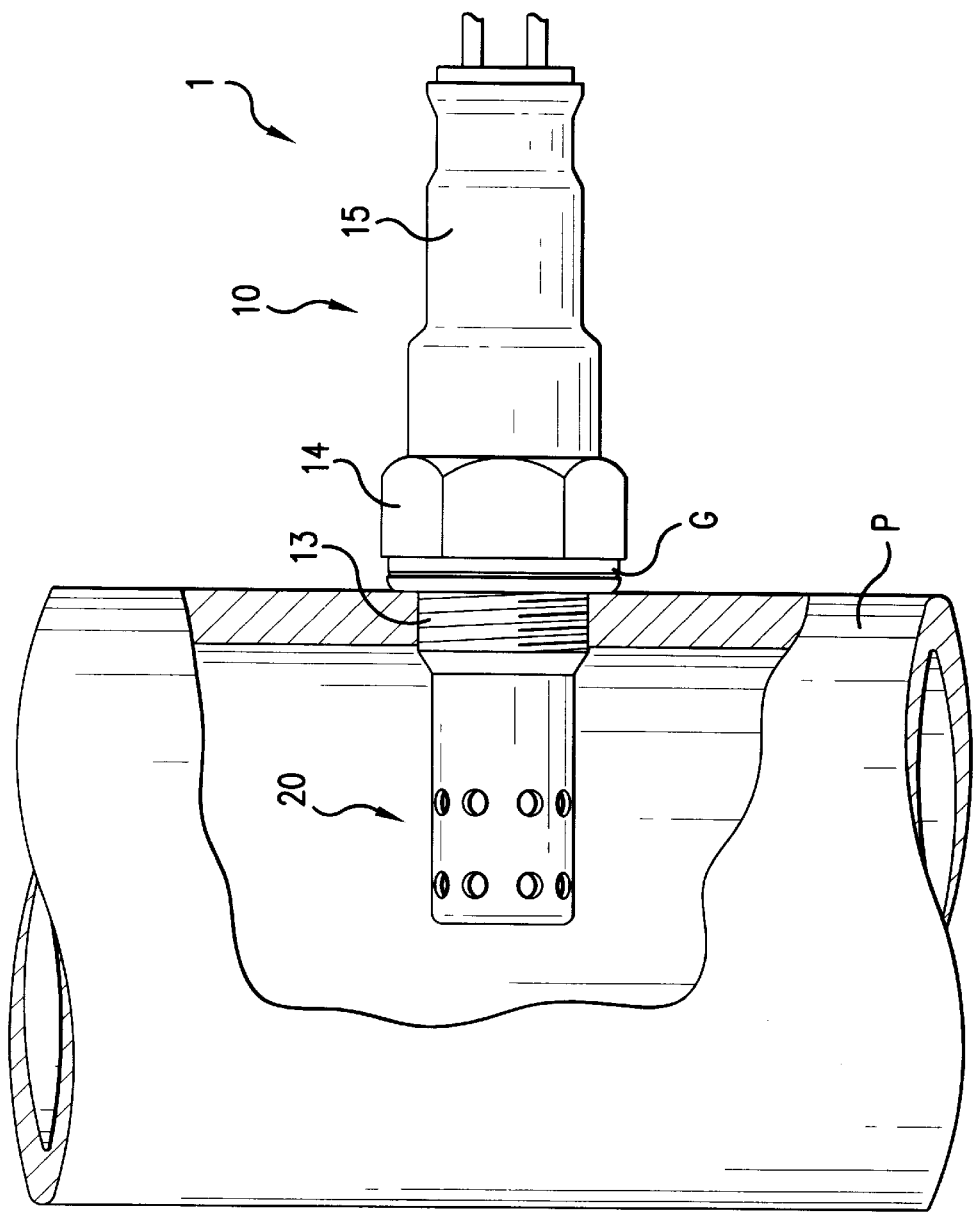
FIG. 1 is a side view of an oxygen sensor of the present invention.

Hereinafter, an embodiment of the present invention will be described with reference to the accompanying drawings. FIG. 1 is a side view of an oxygen sensor of the present invention. An oxygen sensor 1 is composed of a main body unit 10 and a sensor element unit 20 mounted on the main body unit 10. In this figure, symbol G designates a gasket and P is an exhaust passage.

Figure 2:
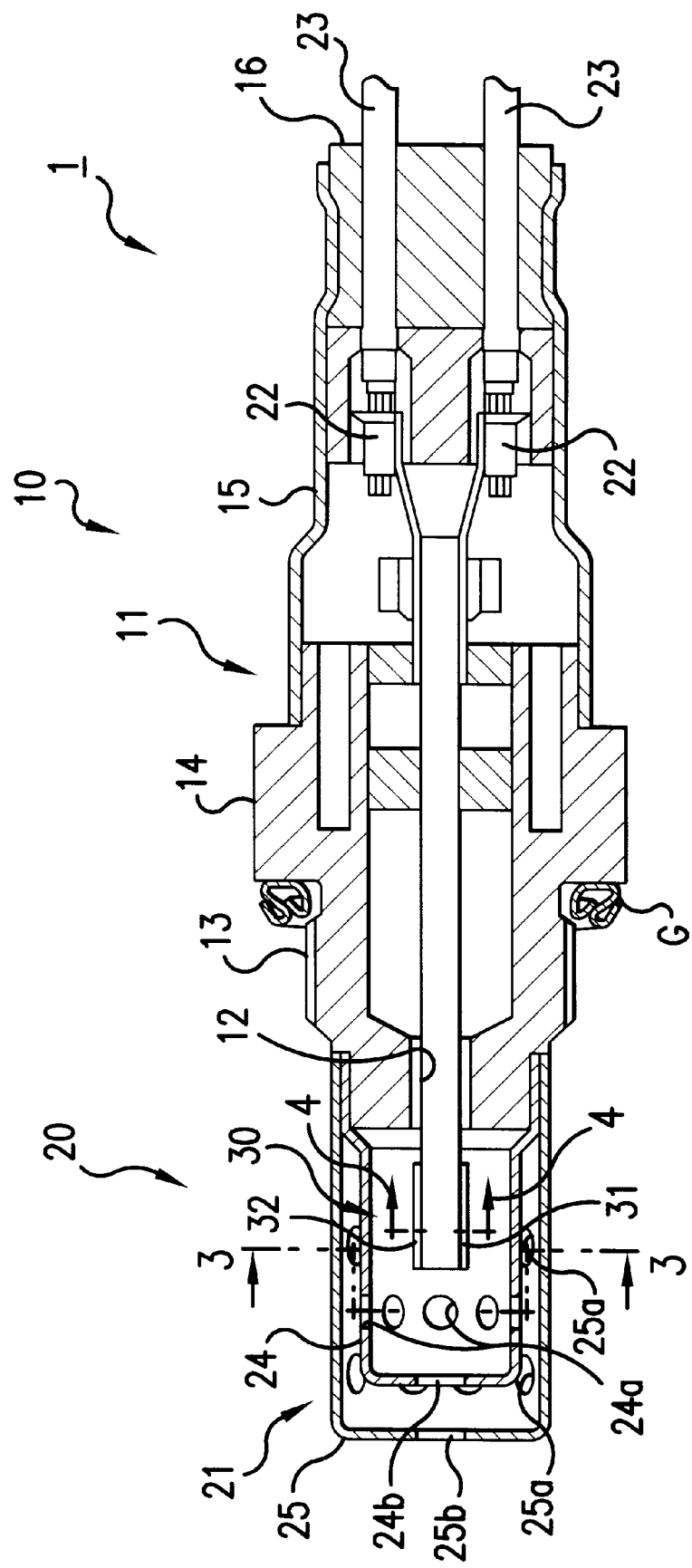
FIG. 2 is a sectional view of the oxygen sensor of the present invention.

FIG. 2 is a sectional view of the oxygen sensor of the present invention. The main body unit 10 includes a main body 11, a hole 12 formed in a central portion of the main body 11, an external thread 13 and a nut portion 14 formed on the main body 11. A pipe 15 is welded to an end portion of the main body 11. A rubber plug 16 is provided that is to be inserted in an opening of the pipe 15 for sealing the opening.

The sensor element unit 20 includes a protector 21 welded to the main body 11 and a detecting element 30 passing through the hole 12 of the main body 11. In this figure, reference numeral 22 designates a terminal crimp and 23 is a lead wire.

The protector 21 includes an inner cylinder 24 and an outer cylinder 25 inserted around the outer periphery of the inner cylinder 24. The inner cylinder 24 has a plurality of gas permeable holes 24a formed in its peripheral wall and a gas permeable hole 24b formed in its leading end plane. The outer cylinder 25 has a plurality of gas permeable holes 25a formed in its peripheral wall and a gas permeable hole 25b formed in its leading end plane.

The detecting element 30 has detecting planes 31 and 32 on which oxygen contained in exhaust gas is to be absorbed. The detail structure of the detecting element 30 will be described in detail later. The orientations of the detecting planes 31 and 32 are determined on the basis of a fastening force applied to the external thread 13 upon mounting of the oxygen sensor 1.

Figure 3:
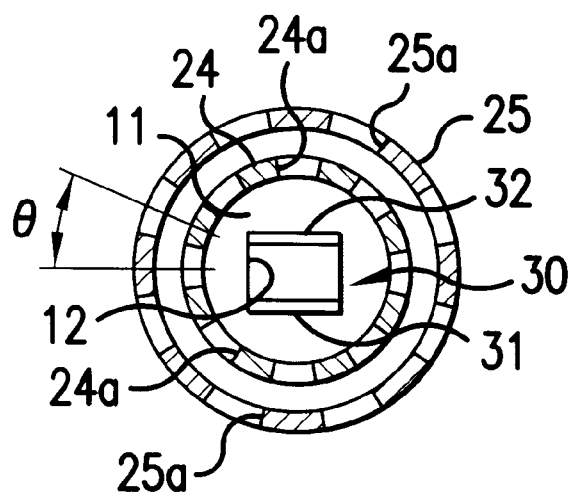
FIG. 3 is a sectional view taken on line 3—3 of FIG. 2.

FIG. 3 is a sectional view taken on line 3—3 of FIG. 2 showing a state in which the detecting element 30 is inserted in the hole 12 formed in the central portion of the main body 11 in such a manner that a space between the detecting plane 31 and the inner wall of the inner cylinder 24 is equal to a space between the detecting plane 32 and the inner wall of the inner cylinder 24.

The plurality of gas permeable holes 24a of the inner cylinder 24 are, in this embodiment, configured as eight circular holes which are spaced at equal intervals along the circumferential direction of the peripheral wall in such a manner that one of the holes 24a faces to each of the detecting planes 31 and 32 of the detecting element 30.

The plurality of gas permeable holes 25a of the outer cylinder 25 are, in this embodiment, configured as eight circular holes shifted from the gas permeable holes 24a by an angle θ.

Figure 4:
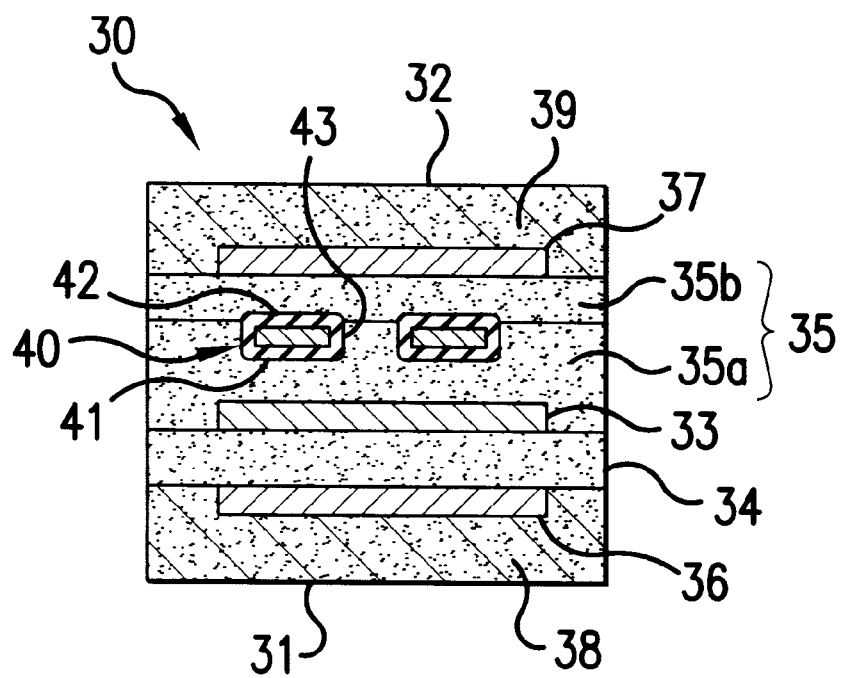
FIG. 4 is a sectional view taken on line 4—4 of FIG. 2.

FIG. 4 is an enlarged sectional view, taken on line 4—4 of FIG. 2, showing the detecting element 30.

Referring to FIG. 4, the detecting element 30 includes a plate-like first electrode 33; a first solid electrolyte layer 34 and a second solid electrolyte layer 35 connected on both sides of the first electrode 33; a second electrode 36 formed on the back surface of the first solid electrolyte layer 34; a third electrode 37 formed on the top surface of the second solid electrolyte layer 35; a protective layer 38 formed to cover the second electrode 36; a protective layer 39 formed to cover the third electrode 37; and a plate heater 40 interposed between the first electrode 33 and the third electrode 37.

The first electrode 33 is formed of a porous platinum (Pt) body having a gas permeability, which is connected to the first and second solid electrolyte layers 34 and 35 for allowing oxygen ions to flow in the first and second solid electrolyte layers 34 and 35.

The second electrode 36 is formed of a porous platinum (Pt) body having a gas permeability, which is connected to the first solid electrolyte layer 34 for allowing oxygen ions to flow in the first solid electrolyte layer 34.

The third electrode 37 is formed of a porous platinum (Pt.) body having a gas permeability, which is connected to the second solid electrolyte layer 35 for alloying oxygen ions to flow in the second solid electrolyte layer 35.

The first solid electrolyte layer 34 is made from stabilized zirconia ($Y_2O_3$—$ZrO_2$ based ceramic) prepared by adding a specific amount of yttria ($Y_2O_3$, yttrium oxide) to a base material, zirconia ($ZrO_2$, zirconium oxide) for stabilization of zirconia.

The second solid electrolyte layer 35 is composed of a first layer 35a and a second layer 35b, each of which is made from stabilized zirconia ($Y_2O_3$—$ZrO_2$ based ceramic) prepared by adding a specific amount of yttria ($Y_2O_3$, yttrium oxide) to a base material, zirconia ($ZrO_2$, zirconium oxide) for stabilization of zirconia.

The plate heater 40 includes a heater main body 41, an insulating layer 42 covering the heater main body 41, and an opening portion 43 formed at a central portion of the plate heater 40. The heater 40 is used to increase the temperature of stabilized zirconia ($Y_2O_3$—$ZrO_2$ based ceramic) over a specific temperature, for example, 300° C. As the temperature of each of the first and second solid electrolyte layers 34 and 35 is increased, the resistance thereof is reduced. That is to say, the resistance of stabilized zirconia ($Y_2O_3$—$ZrO_2$ based ceramic) is dependent on temperature change. In the normal temperature environment of the oxygen sensor, for example, upon start-up of the oxygen sensor, since the resistance of stabilized zirconia is high, it is difficult for the oxygen sensor to detect an oxygen concentration. Accordingly, the starting of detection is made earlier by increasing the temperature of stabilized zirconia by the plate heater 40.

Hereinafter, the shapes of the components of the oxygen sensor and a manufacturing procedure thereof will be described.

Figure 5:
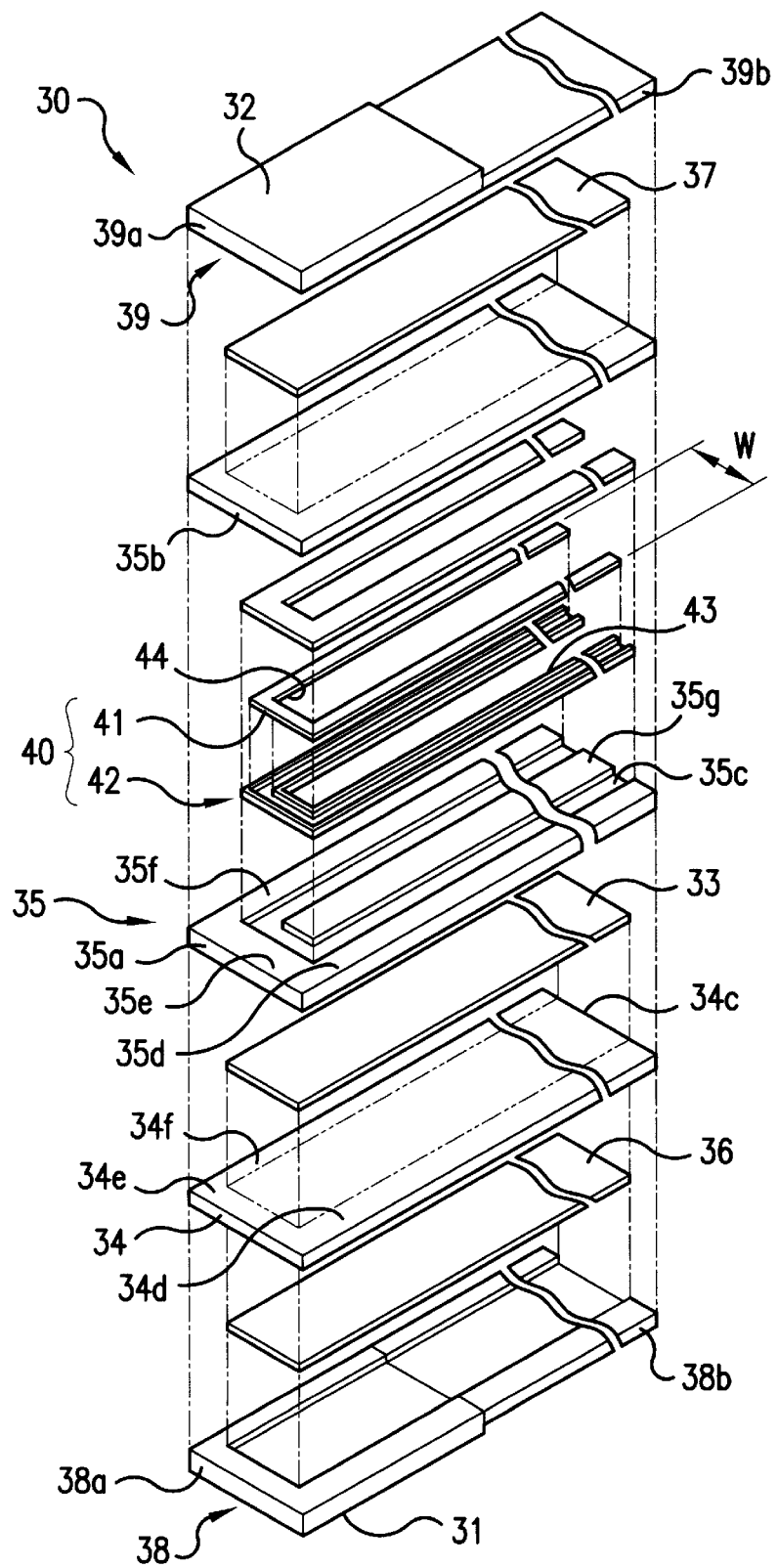
FIG. 5 is an exploded perspective view of a detecting element of the present invention.

FIG. 5 is an exploded perspective view showing respective layers of the detecting element 30 of the present invention. In this figure, although each layer is formed of a thin layer, it is shown on an enlarged scale in the thickness direction for a clearer understanding.

The dimensions of the first, second, and third electrodes 33, 36 and 37 are substantially equal to each other.

The first solid electrolyte layer 34 is composed of a central electrode connection portion 34c, and side connection portions 34d, 34e and 34f, each having a specific width, provided along the edge of the central electrode connection portion 34c. By provision of these connection portions 34d, 34e and 34f, the solid electrolyte layer 34 can be connected to another solid electrolyte layer (second solid electrolyte layer 35) with the first electrode 33 put at the central electrode connection portion 34c therebetween.

The first layer 35a of the second solid electrolyte layer 35 is composed of a heater mounting portion 35c; first connection portions 35d, 35e and 35f, each having a specific width, provided along the edge of the heater mounting portion 35c; and a central second connection portion 35g. By the provision of the first connection portions 35d, 35e and 35f and the second connection portion 35g, the first layer 35a can be connected to another solid electrolyte layer (second layer 35b) with the plate heater 40 put at the heater mounting portion 35c therebetween.

The protective layer 38 is composed of a first protective layer 38a having a gas permeability, and a second protective layer 38b having no gas permeability. To be more specific, the first protective layer 38a is a ceramic film allowing permeation of exhaust gas therethrough, which is provided for preventing deterioration of platinum due to a compound contained in exhaust gas, erosion of platinum due to particles contained in exhaust gas, and separation of platinum due to mechanical impact and/or thermal impact.

The protective layer 39 is composed of a first protective layer 39a having a gas permeability and a second protective layer 39b having no gas permeability. The function of the first protective layer 39a is the same as that of the first protective layer 38a, and therefore, the explanation thereof is omitted.

The heater main body 41 is a plate heater having a width W and provided with an opening 44 at its central portion. The width W is set to be slightly smaller than that of each of the first and second solid electrolyte layers 34 and 35 by a specific dimension. By provision of the opening 44, the first layer 35a can be integrally connected to the second layer 35b over a wide area.

The insulating layer 42 is a film formed on the heater main body 41 to a specific thickness. The film has an opening portion 43 along the opening 44 of the heater main body 41.

One example of a procedure of manufacturing the detecting element 30 will be described below with reference to FIGS. 4 and 5.

The first solid electrolyte layer 34 is prepared by molding stabilized zirconia ($Y_2O_3$—$ZrO_2$ based ceramic) as a raw material into a flat sheet having a specific shape and sintering the sheet in a sintering furnace, for example, a normal pressure tunnel furnace at a temperature of 1300 to 1600° C. The first solid electrolyte layer 34 thus obtained is taken as a substrate, which is additionally machined into a finished shape as needed. Then, the first and second electrodes 33 and 36 composed of thin films, each having a specific thickness, are formed on both sides of the first solid electrolyte layer 34 as the substrate by typically preparing a paint of platinum (Pt), printing both surfaces of the substrate with the Pt paint, and sintering the paint.

The first layer 35a is formed by sintering, and the insulating layer 42, the heater main body 41 and the insulating layer 42 composed of thin films are sequentially formed on the heater mounting portion 35c of the first layer 35a by printing and sistering, to form the plate heater 40. The second layer 35b is formed by sintering, and the third electrode 37 of Pt is formed on the second layer 35b. Then, the first solid electrolyte layer 34, the first layer 35a, the plate heater 40, and the second layer 35b are sequentially stacked in such a manner as to be connected to each other. Finally, the first protective layer 38a is formed on the first solid electrolyte layer 34 and the second electrode 36 by typically thermal-spraying zirconia or alumina ($Al_2O_3$, aluminum oxide) on the first solid electrolyte layer 34 and the second electrode 36, and similarly, the first protective layer 39a is formed on the second solid electrolyte layer 35 and the third electrode 37. The remaining second protective layers 38b and 39b are similarly formed.

The function of the above-described oxygen sensor will be described below.

FIGS. 6(a) and 6(b) are diagrams showing a first function of the oxygen sensor of the present invention, wherein FIG. 6(a) shows the first function of a comparative example, and FIG. 6(b) shows the first function of the embodiment.

Referring to FIG. 6(a), an oxygen sensor 100 is mounted in an exhaust passage in which exhaust gas flows from the upstream side (from the engine side) as shown by hollow arrows 1. The exhaust gas flows in a protector 101 through exhaust gas induction holes 102 formed in the protector 101 as shown by hollow arrows 2, going out of the protector 101 through the exhaust gas induction holes 102 as shown by hollow arrows 3, and flows on the downstream side to be discharged. At this time, the exhaust gas is brought into contact with an outer electrode 106 as shown by arrows 4, whereby an oxygen concentration is detected by a sensor element unit 105 which has a directing angle N extending along only a specific direction within which the responsivity of detection becomes large. Accordingly, when the exhaust gas comes closer to the range of the directing angle N as shown by the hollow arrows 3, the sensor element unit 105 can detect oxygen.

Referring to FIG. 6(b), the oxygen sensor 1 in this embodiment is mounted in an exhaust passage, wherein exhaust gas flows from the upstream side as shown by hollow arrows 5 and enters in the inner cylinder 24 as shown by hollow arrows 6. The exhaust gas flows in the inner cylinder 24 toward the downstream side as shown by hollow arrows 7. At this time, the exhaust gas is brought into contact with the second electrode 36 as shown by arrows 8 and is last brought into contact with the third electrode 37 side as shown by arrows 9. In this embodiment, the oxygen sensor 1 including the second and third electrodes 36 and 37 is advantageous in that the directivity of detection extends in two directions. That is to say, a directing angle E is present on the second electrode 36 side and a directing angle N1 is present on the third electrode 37 side. The directing angle E on the second electrode 36 side is directed on the upstream side, that is, opposite to the flow of the exhaust gas, so that the second electrode 36 is brought in contact with oxygen earlier than the third electrode 37 does and thereby it outputs a detection signal earlier than the third electrode 37 does. On the other hand, the third electrode 37 is located at a position similar to the outer electrode 106 of the comparative example, and it outputs a detection signal when the exhaust gas comes closer to the indicating angle N1 as shown by the hollow arrows 7.

If the third electrode 37 is directed on the upstream side by reversing the orientations of the detecting planes 31 and 32, the third electrode 37 is brought into contact with exhaust gas earlier than the second electrode 36 does and thereby it outputs a detection signal earlier than the second electrode 36 does.

Although the orientations of the second electrode 36 and the third electrode 37 are changed depending on the degree of fastening of the external thread 13 upon mounting of the oxygen sensor 1 (see FIG. 1), the second electrode 36 or third electrode 37 directed on the upstream side, that is, opposite to the flow of the exhaust gas outputs a detection signal earlier than the third electrode 37 or second electrode 36 directed on the downstream side, with a result that the oxygen sensor usually outputs a detection signal for a short response time.

Since the protector 21 is not required to turn exhaust gas between the inner cylinder 24 and the outer cylinder 25, it can be miniaturized. Further, since the gas permeable holes 24a and 25a are formed into simple circular holes, it is possible to reduce the machining cost of the holes 24a and 25a.

In addition, the oxygen sensor in the comparative example is of a type for introducing atmospheric oxygen and detecting an electromotive force on the basis of a difference in oxygen concentration. On the other hand, the oxygen sensor in this embodiment is of a type for detecting an oxygen concentration by applying a voltage to electrodes, and therefore, this type does not require atmospheric air. Accordingly, the oxygen sensor in this embodiment eliminates the necessity of providing any atmospheric air introduction hole.

Figure 7:
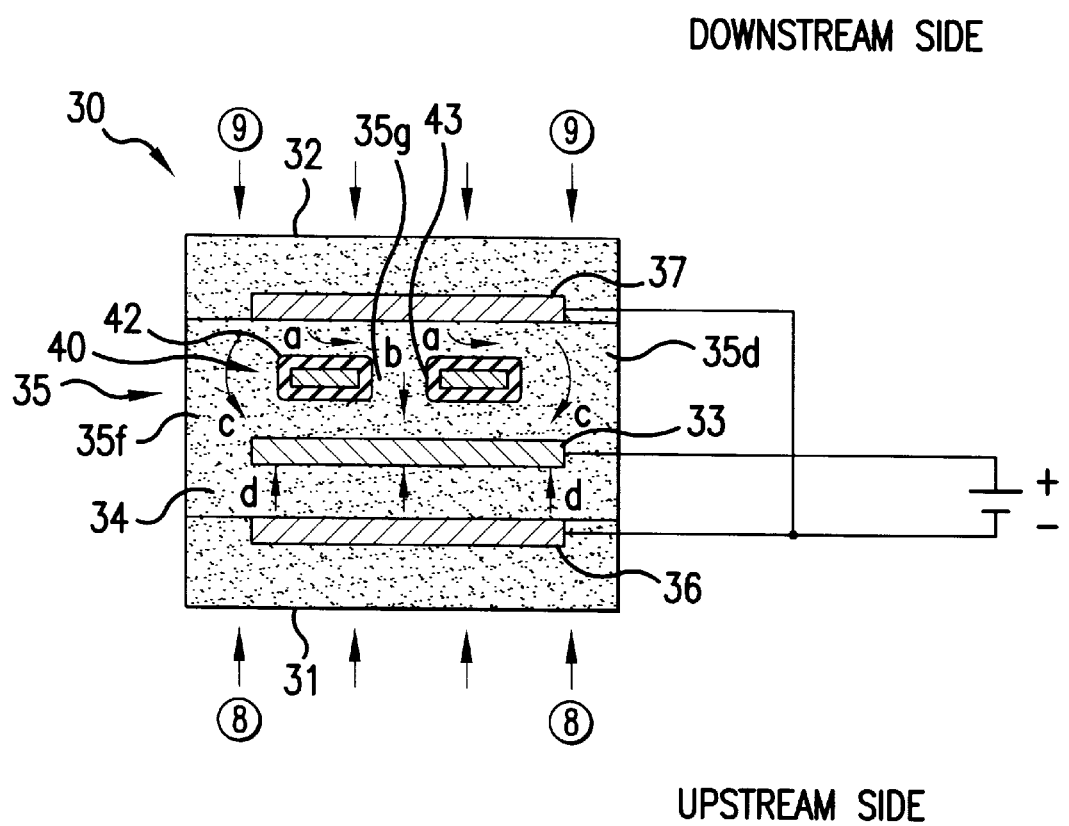
FIG. 7 is a diagram illustrating a second function of the oxygen sensor of the present invention.

FIG. 7 is a diagram showing a second function of the oxygen sensor of the present invention.

Referring to FIG. 7, the exhaust gas is brought into contact with the detecting plane 32 as shown by the arrows 9, and the exhaust gas is brought in contact with the opposed detecting plane 31 as shown by the arrows 8. When an anodic voltage (+) is applied to the central first electrode 33 of the detecting element 30; a cathodic voltage (−) is applied to the second electrode 36; and a cathodic voltage (−) is applied to the third electrode 37, oxygen in the exhaust gas captures electrons by activation of the third electrode 37, to be converted into oxygen ions ($O^{2-}$). The oxygen ions thus generated permeate through the solid electrolyte layer 35 toward the first electrode 33. At this time, the permeation of the oxygen ions is restricted by the insulating layer 42 of the plate heater 40 as shown by arrows "a"; however, in this embodiment, since the opening portion 43 allowing permeation of oxygen ions is formed in the plate heater 40 and the second connection portion 35g is provided on the first layer 35a (see FIG. 5), the oxygen ions pass through the opening portion 43 as shown by an arrow "b", reaching the first electrode 33, and release electrons on the first electrode 33 side to thus remain as oxygen.

Further, since the plate heater 40 having the specific width is buried in the second solid electrolyte layer 35 in the state in which the first side connection portions 35d, 35e and 35f (see FIG. 5) of the second solid electrolyte layer 35, each having the specific width, are protruded from the plate heater 40, the oxygen ions pass through the first connection portions 35d, 35e and 35f as shown by arrows "c", and release electrons on the first electrode 33 side to thus remain as oxygen. In this way, oxygen ions are allowed to pass inside and outside the plate heater 40, so that the detection performance is not reduced although the plate heater 40 is disposed between the first electrode 33 and the third electrode 37.

On the detection plane 31 side, oxygen in the exhaust gas captures electrons by activation of the second electrode 36, to be converted into oxygen ions ($O^{2-}$). The oxygen ions permeate through the solid electrolyte layer 34 as shown by arrows "d", and release electrons on the first electrode 33 side to thus remain as oxygen. A current flows between the electrodes depending on the degree of oxidation/reduction of oxygen, so that a variation in concentration of oxygen in the exhaust gas can be detected as a current value. The application of a voltage for generating oxygen and detection of a current indicating oxygen concentration are carried out by a control unit.

Since the resistance of each of the first and second solid electrolyte layers 34 and 35 is reduced by increasing the temperature of stabilized zirconia ($Y_2O_3$—$ZrO_2$ based ceramic) over a specific temperature, for example, 300° C. by the plate heater 40, it is possible to permit an earlier starting of the detection by the oxygen sensor.

The base material of each of the solid electrolyte layers 34 and 35 described in the embodiment with reference to FIG. 4 is not limited to zirconia ($ZrO_2$) but may be a solid electrolyte [conductive ions: oxygen ions ($O^{2-}$)] such as cerium oxide ($CeO_2$), bismuth oxide ($Bi_2O_3$), hafnium oxide ($HfO_2$), or thorium oxide ($ThO_2$).

The stabilizing agent shown in FIG. 4 is not limited to yttria ($Y_2O_3$) but may be calcium oxide (CaO), magnesium oxide (MgO) or scandium oxide ($Sc_2O_3$).

Although the plate heater 40 shown in FIG. 4 is formed into a flat-plate shape, it may be formed by a wire material, that is, may be formed into any shape allowing permeation of oxygen ions.

In the manufacturing procedure shown in FIG. 4, the solid electrolyte layer 34 is taken as the substrate; however, the solid electrolyte layer 35 may be taken as a substrate and the other components may be sequentially stacked on the substrate.

The present invention having the above configuration exhibits the following effects. According to the present invention, since the second electrode is disposed on one side of the first electrode with a solid electrolyte layer put therebetween and the third electrode is disposed on the other side of the first electrode with a solid electrolyte layer put therebetween, both the sides of the sensor element unit function as detecting planes. This means that the directivity of the oxygen sensor extends in two directions. Since either the second electrode or the third electrode faces to the flow of exhaust gas, the oxygen sensor of the present invention can be brought in contact with exhaust gas earlier than the prior art oxygen sensor does. Accordingly, the response time of the oxygen sensor of the present invention becomes shorter than that of the prior art oxygen sensor.

If the second electrode is directed on the downstream side, the third electrode is directed on the upstream side, and in this case, the third electrode outputs a detection signal earlier than the second electrode does. Accordingly, the detection time of the oxygen sensor of the present invention becomes shorter than that of the prior art oxygen sensor of a type in which detection is performed on the downstream side. As a result, the oxygen sensor of the present invention is improved in terms of the responsivity of detection.

Further, since migration of oxygen ions is detected via the solid electrolyte layers formed on both the sides of the first electrode, each of the second electrode and the third electrode can convert an oxygen concentration into an electric signal. In other words, both the detecting planes of the oxygen sensor can each detect the concentration of oxygen contained in exhaust gas.

Accordingly, the oxygen sensor of the present invention makes it possible to extend the directivity of detection in two directions and to improve the responsivity of detection.

According to the present invention, since the opening portion allowing permeation of oxygen ions therethrough is formed in the plate heater, if the plate heater is disposed on the second electrode side, oxygen ions migrate from the second electrode to the first electrode through the opening portion, to convert an oxygen concentration into an electric signal; while if the plate heater is disposed on the third electrode side, oxygen ions migrate from the third electrode to the first electrode through the opening portion, to convert an oxygen concentration into an electric signal. As a result, although the plate heater is provided between the electrodes, detecting performance is not reduced.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What is claimed is:

1. An oxygen sensor adapted for mounting in an exhaust passage of an engine for detecting an oxygen component contained in exhaust gas, comprising:

a sensor element unit including a first electrode;

a second electrode disposed on one side of said first electrode with a first solid electrolyte layer positioned therebetween, said first solid electrolyte layer is constructed of stabilized zirconia;

a third electrode disposed on the other side of said first electrode with a second solid electrolyte layer positioned therebetween, thereby detecting migration of oxygen ions between said first electrode and said second electrode and migration of oxygen ions between said first electrode and said third electrode, said second electrolyte layer being constructed of two layers, each of said two layers being constructed of stabilized zirconia, one of said two layers including a heater mounting portion; and a plate heater provided in said heater mounting portion.

2. The oxygen sensor according to claim 1, wherein said plate heater has an opening portion allowing permeation of said oxygen ions therethrough, said plate heater being interposed in at least one space, wherein said at least one space is between said first electrode and said third electrode.

3. The oxygen sensor according to claim 2, wherein said plate heater includes a main body and an insulating layer covering entirely the main body with an opened portion formed at a central portion of the plate heater.

4. The oxygen sensor according to claim 1, wherein said first electrode is formed of a porous platinum body having a gas permeability for allowing oxygen ions to flow in the electrolyte layer positioned between the first and second electrodes.

5. The oxygen sensor according to claim 1, wherein said second electrode is formed of a porous platinum body having a gas permeability for allowing oxygen ions to flow in the first electrolyte layer.

6. The oxygen sensor according to claim 1, wherein said third electrode is formed of a porous platinum body having a gas permeability for allowing oxygen ions to flow in the second electrolyte layer.

7. The oxygen sensor according to claim 1, wherein said first electrolyte layer is constructed of sintered stabilized zirconia with a platinum paint sintered thereon.

8. The oxygen sensor according to claim 1, wherein said second electrolyte layer is constructed of sintered stabilized zirconia with a platinum paint sintered thereon.

9. The oxygen sensor according to claim 1, wherein said heater mounting portion further comprises first connection portions each with a specific width provided along an edge of said heater mounting portion.

10. The oxygen sensor according to claim 9, wherein said heater mounting portion further comprises a central second connection portion.

* * * * *